(12) United States Patent
Ku et al.

(10) Patent No.: US 12,297,178 B2
(45) Date of Patent: May 13, 2025

(54) TRIAZOLE DERIVATIVE AND USE THEREOF

(71) Applicant: GYEONGGIDO BUSINESS & SCIENCE ACCELERATOR, Suwon-si (KR)

(72) Inventors: Jin-Mo Ku, Suwon-si (KR); Jin-Kyung In, Yongin-si (KR); Jung-Hun Lee, Suwon-si (KR); Han-Na Cha, Suwon-si (KR)

(73) Assignee: GYEONGGIDO BUSINESS & SCIENCE ACCELERATOR, Suwon-si (KR)

( * ) Notice: Subject to any disclaimer, the term of this patent is extended or adjusted under 35 U.S.C. 154(b) by 0 days.

(21) Appl. No.: 18/395,388

(22) Filed: Dec. 22, 2023

(65) Prior Publication Data

US 2024/0166611 A1 May 23, 2024

Related U.S. Application Data

(63) Continuation of application No. 16/956,010, filed as application No. PCT/KR2017/015056 on Dec. 20, 2017, now abandoned.

(51) Int. Cl.
*C07D 249/06* (2006.01)
*A61P 3/04* (2006.01)

(52) U.S. Cl.
CPC .............. *C07D 249/06* (2013.01); *A61P 3/04* (2018.01)

(58) Field of Classification Search
CPC ................................ C07D 249/06; A61P 3/04
See application file for complete search history.

(56) References Cited

U.S. PATENT DOCUMENTS

2011/0201656 A1* 8/2011 Nardi ..................... A61P 25/16
548/255

FOREIGN PATENT DOCUMENTS

| KR | 10-2007-0065429 A | 6/2007 |
| KR | 10-2010-0046179 A | 5/2010 |
| KR | 10-2011-0022693 A | 3/2011 |
| KR | 10-2011-0050680 A | 5/2011 |

OTHER PUBLICATIONS

Hu, Moleules, 2008, vol. 13, 556-566, ISSN 1420-3049. (Year: 2008).*
International Search Report for PCT/KR2017/015056 dated Sep. 14, 2018 (PCT/ISA/210).
Anderson, Synlett, 2005, No. 19, 2941-2947. (Year: 2005).
Brown, 1998, J Phys Chem A, vol. 102, 8537-8540. (Year: 1998).
Hu, 2008, Molecules, 13, 556-566. (Year: 2008).
Lieber, J Org Chem, 1957, vol. 22, 654-662. (Year: 1957).
Alam, 2006, J Agric Food Chem, 54, 1361-1372. (Year: 2006).
Smith, 1968, J Org Chem, vol. 33(3), 1145-1155. (Year: 1968).
Smith, 1990, J Org Chem, vol. 55, 3351-3362. (Year: 1990).

* cited by examiner

*Primary Examiner* — D Margaret M Seaman
(74) *Attorney, Agent, or Firm* — Sughrue Mion, PLLC

(57) ABSTRACT

The present invention relates to a novel triazole derivative or a salt thereof. The triazole derivative or the salt thereof according to the present invention induces or promotes browning of white adipocytes, and differentiates stem cells, embryonic cells, or preadipocytes to brown adipocytes or beige adipocytes. A composition comprising the triazole derivative or the salt thereof according to the present invention can treat, prevent, or alleviate obesity, obesity complications, diabetes, dyslipidemia, fatty liver, hypertension, metabolic syndrome, and insulin resistance syndrome.

8 Claims, No Drawings

TRIAZOLE DERIVATIVE AND USE THEREOF

CROSS-REFERENCE TO RELATED APPLICATIONS

This application is a Rule 53(b) Continuation of U.S. application Ser. No. 16/956,010 filed Feb. 16, 2021, which is a National Stage of International Application No. PCT/KR2017/015056 filed Dec. 20, 2017, the entire disclosures of which are incorporated herein by reference in their respective entireties.

TECHNICAL FIELD

The present invention relates to a novel triazole derivative or a salt thereof. The triazole derivative or the salt thereof according to the present invention induces or promotes browning of white adipocytes, and differentiates stem cells, embryonic cells, or preadipocytes to brown adipocytes or beige adipocytes. A composition comprising the triazole derivative or the salt thereof according to the present invention can treat, prevent, or alleviate obesity, obesity complications, diabetes, dyslipidemia, fatty liver, hypertension, metabolic syndrome, and insulin resistance syndrome.

BACKGROUND ART

Adipocytes can be classified into white adipocytes, brown adipocytes and beige adipocytes. The white adipocytes serve to store energy in the form of triglycerides. However, if the number of white adipocytes is excessively increased or functional abnormalities occur, it can cause obesity or metabolic related diseases such as diabetes, dyslipidemia, insulin resistance syndrome, fatty liver, etc. On the other hand, the brown adipocytes have a structure containing more mitochondria and small-sized lipid droplets than white adipocytes, and are known to play a role in maintaining body temperature through thermogenic metabolism of these mitochondria.

The process of converting white adipocytes to brown adipocytes after receiving heat-generating stimulation such as cold is called browning. Brown adipocytes in which white adipocytes are converted through the browning process are referred to as beige adipocytes.

The applicant has disclosed a butein or butein derivative in U.S. Patent Publication No. US 2015/0374643 A1 (2015 Dec. 31) as a compound that has a function of inducing brown adipocytes and inducing differentiation from white adipocytes into beige adipocytes.

TECHNICAL PROBLEM

The inventors have performed experiments using various compounds for the purpose of increasing the number of brown adipocytes or beige adipocytes and increasing their cell activities. As a result, it was surprisingly proved that the purpose can be achieved by particular triazole derivative compounds or a pharmaceutically or sitologically acceptable salt thereof, leading to the present invention.

TECHNICAL SOLUTION

The triazole derivative compound according to the present disclosure is represented by a following Formula 1:

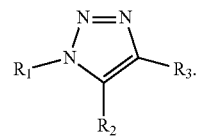

[Formula 1]

In the Formula 1,
—$R_1$ is

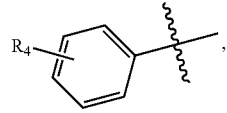

C1-C6 alkyl, C2-C6 alkenyl, C2-C6 alkynyl, C6-C10 aryl, C3-C10 cycloalkyl, or C3-10 heteroaryl or heterocycloalkyl having one or more hetero atoms selected from N, O and S unsubstituted or substituted with $R_5$, $R_4$ is 1 to 5 substituents each independently selected from the group consisting of a hydrogen atom, a halogen atom, C1-C6 alkyl, —$OR_6$, —$O(CO)R_6$, —$NO_2$, —$N(R_6)_2$, —CN, —$COR_6$, —$NH(CO)R_6$, —$NH(CO)NHR_6$, —$NH(CS)NHR_6$, —$NH(SO_2)R_6$, —SH, —$SR_6$, —$SOR_6$, $S(CO)R_6$, —$CO_2R_6$, —$CON(R_6)_2$, —$SO_3H$, —$SO_2N(R_6)_2$ and —$CF_3$, and is bonded to one or more of ortho, meta and para positions, $R_6$ is each independently a hydrogen atom, C1-C6 alkyl, C2-C6 alkenyl, C2-C6 alkynyl, C6-C10 aryl, C3-C10 cycloalkyl,

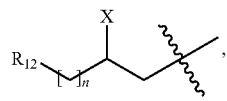

or C3-10 heteroaryl or heterocycloalkyl having one or more hetero atoms selected from N, O and S, $R_{12}$ is —$NHR_{13}$, —$N(R_{13})_2$, —$OR_{13}$,

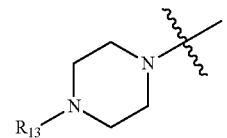

or morpholin, wherein $R_{13}$ is a hydrogen atom or C1-C6 alkyl,

X is a hydrogen atom, $NH_2$ or OH, and n is 0, 1, 2 or 3, $R_5$ is 1 to 5 substituents each independently selected from the group consisting of a hydrogen atom, a halogen atom, C1-C6 alkyl, —$OR_7$, —$O(CO)R_7$, —$NO_2$, —$N(R_7)_2$, —CN, —$COR_7$, —$NH(CO)R_7$, —$NH(CO)NHR_7$, —$NH(CS)NHR_7$, —$NH(SO_2)R_7$, —SH, —$SR_7$, —$SOR_7$, —$S(CO)R_7$, —$CO_2R_7$, —$CON(R_7)_2$, —$SO_3H$, —$SO_2N(R_7)_2$ and —$CF_3$, and is bonded to one or more of ortho, meta and para positions, $R_7$ is each independently a hydrogen atom, C1-C6 alkyl, C2-C6 alkenyl, C2-C6 alkynyl, C6-C10 aryl, C3-C10 cycloalkyl, or C3-10 heteroaryl or heterocycloalkyl having one or more hetero atoms selected from N, O and S;

—$R_2$ is a hydrogen atom or $NH_2$;

—$R_3$ is

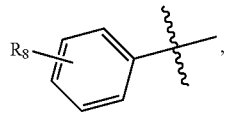

C1-C6 alkyl, C2-C6 alkenyl, C2-C6 alkynyl, C6-C10 aryl, C3-C10 cycloalkyl, or C3-10 heteroaryl or heterocycloalkyl having one or more hetero atoms selected from N, O and S unsubstituted or substituted with $R_9$, $R_8$ is 1 to 5 substituents each independently selected from the group consisting of a hydrogen atom, a halogen atom, C1-C6 alkyl, —$OR_{10}$, —$O(CO)R_{10}$, —$NO_2$, —$N(R_{10})_2$, —CN, —$COR_{10}$, —$NH(CO)R_{10}$, —NH(CO)NHR$_{10}$, —NH(CS)NHR$_{10}$, —NH(SO$_2$)R$_{10}$, —SH, —SR$_{10}$, —SOR$_{10}$, —S(CO)R$_{10}$, —CO$_2$R$_{10}$, —CON(R$_{10}$)$_2$, —SO$_3$H, —SO$_2$N(R$_{10}$)$_2$ and —CF$_3$, and is bonded to one or more of ortho, meta and para positions, $R_{10}$ is each independently a hydrogen atom, C1-C6 alkyl, C2-C6 alkenyl, C2-C6 alkynyl, C6-C10 aryl, C3-C10 cycloalkyl,

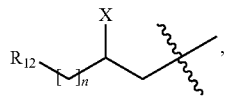

or C3-10 heteroaryl or heterocycloalkyl having one or more hetero atoms selected from N, O and S, $R_{12}$ is —NHR$_{13}$, —N(R$_{13}$)$_2$, —OR$_{13}$,

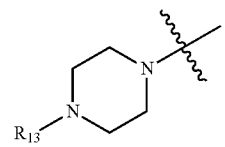

or morpholin, wherein $R_{13}$ is a hydrogen atom or C1-C6 alkyl,

X is a hydrogen atom, NH$_2$ or OH, and n is 0, 1, 2 or 3, $R_9$ is 1 to 5 substituents each independently selected from the group consisting of a hydrogen atom, a halogen atom, C1-C6 alkyl, —OR$_{11}$, —O(CO)R$_{11}$, —NO$_2$, —N(R$_{11}$)$_2$, —CN, —COR$_{11}$, —NH(CO)R$_{11}$, —NH(CO)NHR$_{11}$, —NH(CS)NHR$_{11}$, —NH(SO$_2$)R$_{11}$, —SH, SR$_{11}$, —SOR$_{11}$, —S(CO)R$_{11}$, —CO$_2$R$_{11}$, —CON(R$_{11}$)$_2$, —SO$_3$H, —SO$_2$N(R$_{11}$)$_2$ and —CF$_3$, and is bonded to one or more of ortho, meta and para positions, $R_{11}$ is each independently a hydrogen atom, C1-C6 alkyl, C2-C6 alkenyl, C2-C6 alkynyl, C6-C10 aryl, C3-C10 cycloalkyl, or C3-10 heteroaryl or heterocycloalkyl having one or more hetero atoms selected from N, O and S.

In a preferred embodiment, the compound is represented by a following Formula 2:

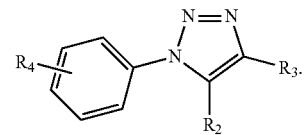

In the Formula 2, $R_2$, $R_3$ and $R_4$ are as defined above.

In a preferred embodiment, the compound is represented by a following Formula 3:

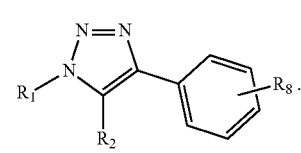

In the Formula 3, $R_1$, $R_2$ and $R_8$ are as defined above.

In a more preferred embodiment, the compound or salt thereof is selected from the group consisting of:

4-(1-(2,4-dimethoxyphenyl)-1H-1,2,3-triazole-4-yl)benzene-1,2-diol;
4-(1-(4-chlorophenyl)-1H-1,2,3-triazole-4-yl)benzene-1,2-diol;
4-(1-(4-fluorophenyl)-1H-1,2,3-triazole-4-yl)benzene-1,2-diol;
4-(1-(4-hydroxyphenyl)-1H-1,2,3-triazole-4-yl)benzene-1,2-diol;
4-(1-(4-hydroxy-3-methylphenyl)-1H-1,2,3-triazole-4-yl)benzene-1,2-diol;
(E)-N-(4-chlorophenethyl)-3-(3,4-dihydroxyphenyl)acrylamide;
4-(1-(3-fluoro-4-hydroxyphenyl)-1H-1,2,3-triazole-4-yl)benzene-1,2-diol;
4-(1-(3,4-difluorophenyl)-1H-1,2,3-triazole-4-yl)benzene-1,2-diol;
4-(1-(2-fluoro-4-hydroxyphenyl)-1H-1,2,3-triazole-4-yl)benzene-1,2-diol;
4-(1-(4-fluoro-3-hydroxyphenyl)-1H-1,2,3-triazole-4-yl)benzene-1,2-diol;
4-(1-(3-fluorophenyl)-1H-1,2,3-triazole-4-yl)benzene-1,2-diol;
4-(1-(3-fluoro-4-methoxyphenyl)-1H-1,2,3-triazole-4-yl)benzene-1,2-diol;
4-(1-(2-fluorophenyl)-1H-1,2,3-triazole-4-yl)benzene-1,2-diol;
4-(1-(2,3-difluoro-4-hydroxyphenyl)-1H-1,2,3-triazole-4-yl)benzene-1,2-diol;
4-(1-(4-(2-hydroxyethoxy)phenyl)-1H-1,2,3-triazole-4-yl)benzene-1,2-diol;
4-(1-(4-(2-(dimethylamino)ethoxy)phenyl)-1H-1,2,3-triazole-4-yl)benzene-1,2-diol hydrochloride;
4-(1-(4-(3-(dimethylamino)-2-hydroxypropoxy)phenyl)-1H-1,2,3-triazole-4-yl)benzene-1,2-diol hydrochloride;
N-(2-(diethylamino)ethyl)-4-(4-(3,4-dihydroxyphenyl)-1H-1,2,3-triazole-1-yl)benzamide hydrochloride;
N-(3-(diethylamino)propyl)-4-(4-(3,4-dihydroxyphenyl)-1H-1,2,3-triazole-1-yl)benzamide hydrochloride;
1-(3,4-dimethoxyphenyl)-4-phenyl-1H-1,2,3-triazole-5-amine;
4-(5-amino-4-phenyl-1H-1,2,3-triazole-1-yl)benzene-1,2-diol;

4-(benzo[d][1,3]dioxol-5-yl)-1-(3,4-dimethoxyphenyl)-1H-1,2,3-triazole-5-amine;
4-(4-chlorophenyl)-1-(3,4-dimethoxyphenyl)-1H-1,2,3-triazole-5-amine;
4-(5-amino-4-(4-chlorophenyl)-1H-1,2,3-triazole-1-yl)benzene-1,2-diol;
4-(5-amino-1-(4-chlorophenyl)-1H-1,2,3-triazole-4-yl)benzene-1,2-diol; and
4-(5-amino-1-(3,4-dihydroxyphenyl)-1H-1,2,3-triazole-4-yl)-N-(2-(diethylamino)ethyl)benzamide hydrochloride.

In an even more preferred embodiment, the compound or salt thereof is selected from the group consisting of:
4-(1-(2,4-dimethoxyphenyl)-1H-1,2,3-triazole-4-yl)benzene-1,2-diol;
4-(1-(4-chlorophenyl)-1H-1,2,3-triazole-4-yl)benzene-1,2-diol;
4-(1-(4-fluorophenyl)-1H-1,2,3-triazole-4-yl)benzene-1,2-diol;
4-(1-(4-hydroxyphenyl)-1H-1,2,3-triazole-4-yl)benzene-1,2-diol;
4-(1-(4-hydroxy-3-methylphenyl)-1H-1,2,3-triazole-4-yl)benzene-1,2-diol;
4-(1-(4-(2-hydroxyethoxy)phenyl)-1H-1,2,3-triazole-4-yl)benzene-1,2-diol;
4-(1-(4-(2-(dimethylamino)ethoxy)phenyl)-1H-1,2,3-triazole-4-yl)benzene-1,2-diol hydrochloride; and
4-(5-amino-4-(4-chlorophenyl)-1H-1,2,3-triazole-1-yl)benzene-1,2-diol.

In the present disclosure, terms such as alkyl, alkenyl, alkynyl are meant to include both linear or branched types.

The term "halogen" as used in the present disclosure means fluorine, chlorine, bromine or iodine.

The term "each independently" as used in the present disclosure means that two or more substituents selected in the group may be different from each other or may be the same.

Since the compounds of Formula 1 may have an asymmetric carbon center, it may exist as an R or S isomer, a racemate, a diastereomer, or a mixture thereof, all of which are included in the scope of the present disclosure.

The term "pharmaceutically or sitologically acceptable salt" used in the present disclosure is a salt that can be prepared by a method conventional in the art, for example, but are not limited to, a pharmaceutically or sitologically acceptable acid addition salt formed with inorganic acids such as hydrochloric acid, hydrogen bromide, sulfuric acid, sodium hydrogen sulfate, phosphoric acid, carbonic acid, or with organic acids such as formic acid, acetic acid, oxalic acid, benzoic acid, citric acid, tartaric acid, gluconic acid, gastisic acid, fumaric acid, lactobionic acid, salicylic acid, or acetylsalicylic acid (aspirin), a pharmaceutically or sitologically acceptable metal salt formed by reacting with alkali metal ions such as sodium and potassium, or a pharmaceutically or sitologically acceptable salt formed by reacting with ammonium ions.

The present disclosure provides a composition for inducing or promoting browning of white adipocytes, comprising a compound represented by Formula 1 or a pharmaceutically or sitologically acceptable salt thereof as an active ingredient.

The browning generally refers to a process in which white adipocytes are converted into brown adipocytes after being stimulated to generate heat. Therefore, in order to proceed with the browning process, a heat-generating stimulation such as cold is required above a certain level. However, when the composition according to the present disclosure is administered, the browning process of white adipocytes can be induced or promoted even if there is no or little heat-generating stimulation. As a result, the white adipocytes are transdifferentiated into beige adipocytes or brown adipocytes. Here, the term transdifferentiation refers to a phenomenon in which completely differentiated cells or progeny cells produced by division thereof undergo different differentiation.

The effect of inducing or promoting browning of white adipocytes exhibited by the composition according to the present disclosure can be obtained both in vitro and in vivo when administered to a subject. When the composition according to the present disclosure is administered, the number of white adipocytes decreases, while the number of brown adipocytes increases due to the browning process.

In another aspect, the present disclosure provides a composition for inducing or promoting differentiation of stem cells, embryonic cells or preadipocytes into brown adipocytes or beige adipocytes, comprising a compound represented by Formula 1 or a pharmaceutically or sitologically acceptable salt thereof as an active ingredient Stem cells, embryonic cells, or preadipocytes may be differentiated into white adipocytes or otherwise into brown adipocytes or beige adipocytes depending on factors such as surrounding environment or stimulus. However, when the composition according to the present disclosure is administered, the process of differentiation into brown adipocytes or beige adipocytes is induced or promoted. As a result, the number of brown adipocytes or beige adipocytes in adipose tissue is increased to a significant level, and accordingly, intrinsic activity such as heat generation or body temperature maintenance action can be efficiently increased.

The effect of inducing or promoting differentiation of stem cells, embryonic cells or preadipocytes into brown adipocytes or beige adipocytes which is exhibited by the composition according to the present disclosure can be obtained both in vitro and in vivo when administered to a subject.

The content of triazole derivative comprised as an active ingredient in the composition of the present disclosure can be appropriately determined by a person skilled in the art or a skilled physician considering various factors such as the age, sex, weight and health status of the subject, the severity of obesity or complications or metabolic diseases, the onset time, the treatment period, the route of administration, etc. For example, the content of the triazole derivative may be 0.001 to 100% by weight based on the total weight of the composition.

The daily dosage of the composition according to the present disclosure can be appropriately determined by a person skilled in the art or a skilled physician in consideration of various factors such as the age, sex, weight and health condition of the subject, the severity of obesity or complications or metabolic disease, the onset time, the treatment period, and the route of administration. For example, the daily dosage of the composition according to the present disclosure may be an amount of 1 to 500 mg per kg of body weight of the subject. The daily dosage may be divided into once or several times a day, and administered to the subject. Alternatively, the composition according to the present disclosure may be administered once or several times a week, once or several times a month, once or several times a year, and the administration cycle may be appropriately selected by a person skilled in the art or a skilled physician.

In the present disclosure, the term "subject" refers to animals including humans and mammals. Preferably, the subject is a human. In particular, the subject may be a human in which the number of white adipocytes is present in an excess amount compared to the normal level, or a human who already suffers or is likely to suffer from obesity or complications such as diabetes, dyslipidemia, high blood pressure, metabolic syndrome, fatty liver, etc.

The composition according to the present disclosure may be a pharmaceutical composition or a food composition.

The pharmaceutical composition is provided for use in the treatment or prevention of one or more selected from the group consisting of obesity, obesity complications, diabetes, dyslipidemia, fatty liver, hypertension, metabolic syndrome and insulin resistance syndrome. The food composition is provided for use for the alleviation or prevention of one or more selected from the group consisting of obesity, obesity complications, diabetes, dyslipidemia, fatty liver, hypertension, metabolic syndrome and insulin resistance syndrome.

The term "treatment" or "treating" as used in the present disclosure refers to any action in which a disease or abnormal symptom is improved or cured by administration of the composition according to the present disclosure. The term "prevention" or "preventing" as used in the present disclosure means any action in which a disease or abnormal symptom is suppressed or delayed by administration of the composition according to the present disclosure. The term "alleviation" or "alleviating" as used in the present disclosure means any action in which the degree of disease or abnormal symptom is reduced, improved, or progression is delayed by administration of the composition according to the present disclosure.

The composition according to the present disclosure can be administered to a subject by a variety of routes which are pharmaceutically or sitologically acceptable. For example, it may be administered by oral, topical, intraperitoneal, subcutaneous or intravenous injection, but not limited thereto. When the composition according to the present disclosure is provided in the form of food or food supplement, it is generally administered orally to a subject.

The composition according to the present disclosure is not limited to a specific dosage form, and may be formulated into various oral or parenteral dosage forms. The active ingredient may be contained in a unit dose or divided into aliquots in the formulation. When formulating the composition according to the present disclosure, it can additionally comprise various additives such as pharmaceutically or sitologically acceptable conventional plasticizers, excipients, disintegrants, fillers, extenders, binders, lubricants, coloring agents, wetting agents, sweetening agents, fragrances, preservatives, surfactants, diluents, antioxidants, etc. Solid formulations for oral administration may be, for example, tablets, pills, powders, granules, capsules, etc., and may comprise one or more excipients such as starch, calcium carbonate, sucrose, lactose or gelatin. Liquid formulations for oral administration may be, for example, suspensions, liquid solutions, emulsions, syrups, etc., and may comprise various excipients such as humectants, sweeteners, fragrances, preservatives as well as water, liquid paraffin as diluents commonly used. Formulations for parenteral administration may be, for example, sterilized aqueous solutions, non-aqueous agents, suspensions, emulsions, lyophilized formulations, suppositories, and the like. As the suspending agent, propylene glycol, polyethylene glycol, vegetable oil such as olive oil, injectable ester such as ethyl oleate, and the like may be used. In addition, when the composition according to the present disclosure is used as food, it may additionally comprise food additives widely used in the art such as flavoring agents and vitamins.

In an another embodiment, the composition of the present disclosure may additionally comprise other active ingredients or differentiation inducing agents which are known in the art to induce or promote browning of white adipocytes, and/or differentiation of stem cells, embryonic cells or preadipocytes into brown adipocytes or beige adipocytes, as long as they do not inhibit the effect of the active ingredient of the present disclosure or cause side effects.

EXAMPLES

In the following, exemplary embodiments of the inventive concept will be explained in further detail with reference to examples. However, the following examples are meant to exemplify the present invention, and the scope of the invention is not restricted by these examples. In addition, those skilled in the art will be able to make various modifications to the present invention within the scope not departing from the inventive concept.

Examples of preparation of compounds of Formula 1 according to the present disclosure are described below. Representative examples corresponding thereto along with specific preparation steps are described below. Compounds having different substituents were prepared through similar steps, but not all examples are described here. Referring to the following representative examples, those skilled in the art will be able to easily prepare compounds of Formula 1 or salts thereof having different substituents.

Preparation Example 1

1-1. Preparation of the Compound of Formula 1 Based on Chemical Equation 1

Compounds 1 to 14 belonging to Formula 1 of the present disclosure can be prepared according to the following Chemical Equation 1:

[Chemical Equation 1]

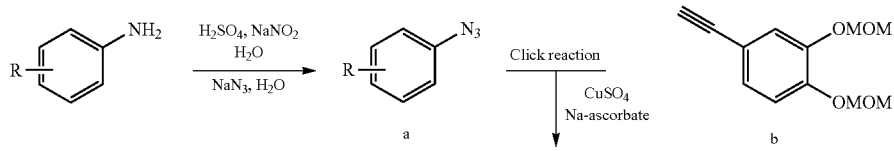

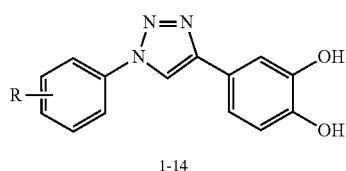
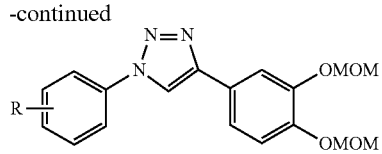

R =
1: 2,4-OMe
2: 4-Cl
3: 4-F
4: 4-OH
5: 3-Me, 4-OH
6: 4-COOH
7: 3-F, 4-OH
8 : 3,4-F
9 : 2-F, 4-OH
10: 3-OH, 4-F
11: 3-F
12: 3-F, 4-OMe
13: 2-F
14: 2,3-F, 4-OH

Compound c can be obtained by Click reaction from Compound a and Compound b prepared through commonly known methods. More specifically, it can be obtained by adding a catalytic amount of Cu ion and a reducing agent (for example, sodium ascorbate) under a certain ratio of water and quaternary butyl alcohol solvent conditions, and performing the reaction for 8 to 24 hours at room temperature. An aqueous acid solution such as hydrochloric acid is added to the obtained triazole Compound c under methanol solvent conditions, and the protecting groups are deprotected at room temperature or 50° C. to obtain the final products Compounds 1 to 14.

1-2. Preparation of Compound 3 Based on Chemical Equation 1

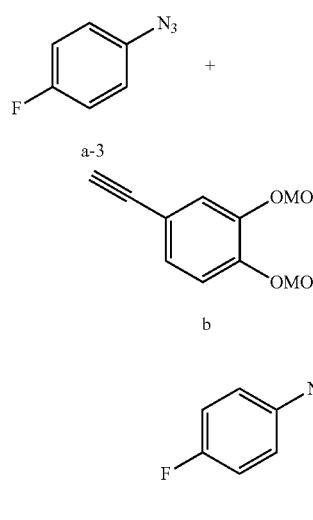

4-fluorophenyl azide (a-3) (100 mg, 0.73 mmol) and 4-ethynyl-1,2-beads (methoxymethoxy)benzene (b) (162 mg, 0.73 mmol) that can be easily prepared by conventional methods were dissolved in a solvent of a 1:1 ratio of quaternary butyl alcohol and water (2 mL/2 mL). And then, cooper sulfate (11 mg, 0.073 mmol) and sodium ascorbate (28 mg, 0.146 mmol) were added, and stirred for 12 hours at room temperature. After checking the completion of the reaction, extraction was performed using ethyl acetate (10 mL×2) and distilled water (10 mL). The extracted organic layer was dried with anhydrous sodium sulfate, filtered, and then distilled under reduced pressure. And, the filtrate was purified under normal phase column conditions (ethyl acetate:hexane=2:1). Compound c-3 was obtained in the form of a light beige solid (195 mg, 73% yield).

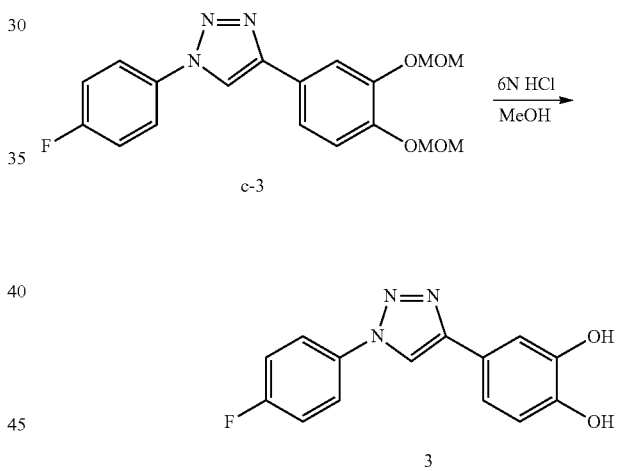

After dissolving the prepared Compound c-3 (100 mg, 0.28 mmol) in methyl alcohol (2 ml), 6N hydrochloric acid (0.2 ml) was added. And, the temperature was raised to 50° C., and stirred for 1 hour. After checking the completion of the reaction, it was cooled at room temperature and methyl alcohol was distilled under reduced pressure to obtain a yellow solid. After washing the obtained solid with hexane, it was purified by recrystallization using a small amount of methyl alcohol. As a result, Compound 3 was obtained in the form of a beige solid (78 mg, 91% yield).

The chemical structure and identification data of Compounds 1 to 14 obtained are as follows.

Compound 1: 4-(1-(2,4-dimethoxyphenyl)-1H-1,2,3-triazole-4-yl)benzene-1.2-diol

Compound 1 was obtained in the form of a white solid, and its chemical structure and identification data are as follows:

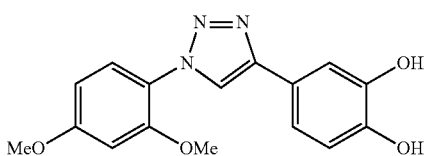 [SMILES: COc1ccc(-n2cc(-c3ccc(O)c(O)c3)nn2)c(OC)c1]

¹H NMR 400 MHZ (MeOD): δ 8.34(s, 1H), 7.54(d, J=8.0 Hz, 1H), 7.31(s, 1H), 7.20(d, J=8.4 Hz, 1H), 6.85(d, J=8.4 Hz 1H), 6.81(s, 1H), 6.71(d, J=8.4Hz, 1H), 3.90(s, 6H);

Mass (m/z) [M+H]⁺: 314.3.

Compound 2: 4-(1-(4-chlorophenyl)-1H-1,2,3-triazole-4-yl)benzene-1,2-diol

Compound 2 was obtained in the form of a beige solid, and its chemical structure and identification data are as follows:

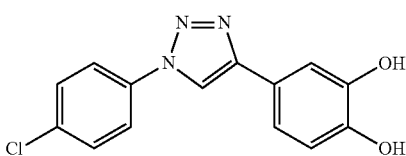 [SMILES: Oc1ccc(-c2cn(-c3ccc(Cl)cc3)nn2)cc1O]

¹H NMR 400 MHZ (MeOD): δ 8.79(s, 1H), 7.95(d, J=8.8 Hz, 2H), 7.64(d, J=8.8 Hz, 2H), 7.36(d, J=1.6 Hz, 1H), 7.25(dd, J=8.0, 2.0 Hz, 1H), 6.88(d, J=8.0 Hz, 1H);

Mass (m/z) [M+H]⁺: 288.7.

Compound 3: 4-(1-(4-fluorophenyl)-1H-1,2,3-triazole-4-yl)benzene-1,2-diol

Compound 3 was obtained in the form of a beige solid, and its chemical structure and identification data are as follows:

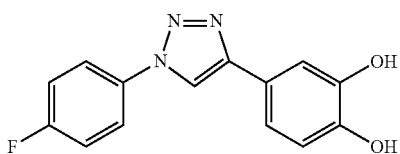 [SMILES: Oc1ccc(-c2cn(-c3ccc(F)cc3)nn2)cc1O]

¹H NMR 400 MHZ (MeOD): δ 8.75(s, 1H), 7.96(dd, J=9.2, 4.8 Hz, 2H), 7.34-7.41(m, 3H), 7.25(dd, J=8.4, 2.0 Hz, 1H), 6.88(d, J=8.4 Hz, 1H);

Mass (m/z) [M+H]⁺: 272.3.

Compound 4: 4-(1-(4-hydroxyphenyl)-1H-1,2,3-triazole-4-yl)benzene-1,2-diol

Compound 4 was obtained in the form of a yellow solid, and its chemical structure and identification data are as follows:

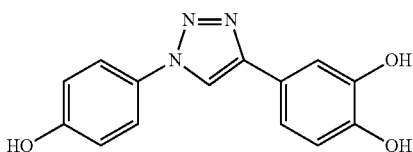 [SMILES: Oc1ccc(-n2cc(-c3ccc(O)c(O)c3)nn2)cc1]

¹H NMR 400 MHZ (MeOD): δ 8.94(s, 1H), 7.76(d, J=8.0 Hz, 2H), 7.33(s, 1H), 7.24(d, J=8.4 Hz, 1H), 7.02(d, J-8.4 Hz, 2H), 6.92(d, J=8.4 Hz, 1H);

Mass (m/z) [M+H]⁺: 270.3.

Compound 5: 4-(1-(4-hydroxy-3-methylphenyl)-1H-1,2,3-triazole-4-yl)benzene-1,2-diol Compound 5 was obtained in the form of a brown solid, and its chemical structure and identification data are as follows:

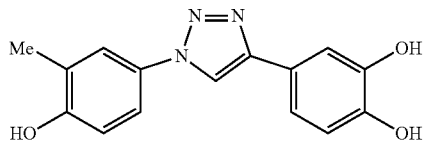 [SMILES: Cc1cc(-n2cc(-c3ccc(O)c(O)c3)nn2)ccc1O]

¹H NMR 400 MHZ (MeOD): δ 8.53(s, 1H), 7.59(d, J=2.4 Hz, 1H), 7.49(dd, J=8.4, 2.4 Hz, 1H), 7.33(d, J=2.0 Hz, 1H), 7.22(dd, J=8.0, 2.0 Hz, 1H), 6.92(d, J=8.4 Hz, 1H), 6.86(d, J=8.4 Hz, 1H), 2.30(s, 3H);

Mass (m/z) [M+H]⁺: 284.3.

Compound 6: (E)-N-(4-chlorophenethyl)-3-(3,4-dihydroxyphenyl)acrylamide

Compound 6 was obtained in the form of a white solid, and its chemical structure and identification data are as follows:

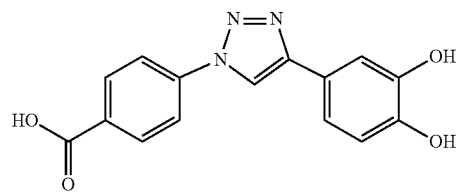 [SMILES: O=C(O)c1ccc(-n2cc(-c3ccc(O)c(O)c3)nn2)cc1]

¹H NMR 400 MHZ (MeOD): δ 8.85(s, 1H), 8.26(d, J=8.8 Hz, 2H), 8.08(d, J=8.8 Hz, 2H), 7.38(d, J=2.0 Hz, 1H), 7.27(dd, J=8.4, 2.4 Hz, 1H), 6.88(d, J=8.4 Hz, 1H);

Mass (m/z) [M+H]⁺: 298.3.

Compound 7: 4-(1-(3-fluoro-4-hydroxyphenyl)-1H-1,2,3-triazole-4-yl)benzene-1,2-diol Compound 7 was obtained in the form of a beige solid, and its chemical structure and identification data are as follows:

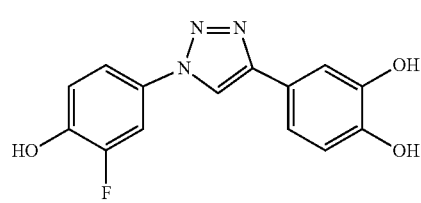 [SMILES: Oc1ccc(-c2cn(-c3ccc(O)c(F)c3)nn2)cc1O]

¹H NMR 400 MHZ (MeOD): δ 8.77(s, 1H), 7.72(dd, J=11.6, 2.8 Hz, 1H), 7.55-7.62(m, 1H), 7.33(d, J=2.0 Hz, 1H), 7.23(dd, J=8.0, 2.0 Hz, 1H), 7.14(t, J=8.4 Hz, 1H), 6.89(d, J-8.4Hz, 1H);

Mass (m/z) [M+H]⁺: 288.3.

Compound 8: 4-(1-(3,4-difluorophenyl)-1H-1,2,3-triazole-4-yl)benzene-1,2-diol

Compound 8 was obtained in the form of a beige solid, and its chemical structure and identification data are as follows:

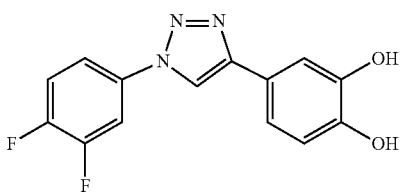 [SMILES: Oc1ccc(-c2cn(-c3ccc(F)c(F)c3)nn2)cc1O]

¹H NMR 400 MHZ (MeOD): δ 8.80(s, 1H), 7.95-8.02(m, 1H), 7.76-7.83(m, 1H), 7.55(d, J=18.4, 8.4 Hz, 1H), 7.35(d, J=2.4 Hz, 1H), 7.24(dd, J=8.0, 2.0 Hz, 1H), 6.88(d, J=8.0 Hz, 1H);

Mass (m/z) [M+H]⁺: 290.2.

Compound 9: 4-(1-(2-fluoro-4-hydroxyphenyl)-1H-1,2,3-triazole-4-yl)benzene-1,2-diol Compound 9 was obtained in the form of a brown solid, and its chemical structure and identification data are as follows:

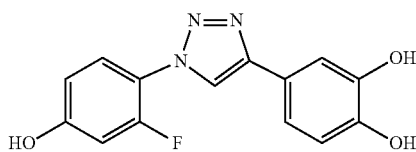 [SMILES: Oc1ccc(-n2cc(-c3ccc(O)c(O)c3)nn2)c(F)c1]

¹H NMR 400 MHZ (MeOD): δ 8.43(s, 1H), 7.99(s, 1H), 7.60(t, J=8.0 Hz, 1H), 7.33(s, 1H), 7.22(d, J=8.4 Hz, 1H), 7.86(d, J=8.0 Hz, 1H), 6.81(d, J=10.4 Hz, 1H);

Mass (m/z) [M+H]⁺: 288.3.

Compound 10: 4-(1-(4-fluoro-3-hydroxyphenyl)-1H-1,2,3-triazole-4-yl)benzene-1,2-diol Compound 10 was obtained in the form of an ocher solid, and its chemical structure and identification data are as follows:

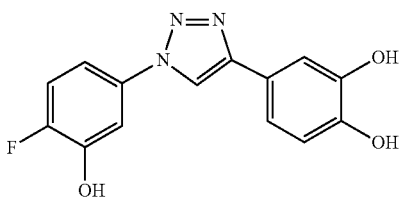 [SMILES: Oc1ccc(-c2cn(-c3ccc(F)c(O)c3)nn2)cc1O]

¹H NMR 400 MHZ (MeOD): δ 8.80(s, 1H), 7.52(d, J=7.2 Hz, 1H), 7.28-7.39(m, 3H), 7.24(d, J=8.0 Hz, 1H), 6.89(d, J=8.4 Hz, 1H);

Mass (m/z) [M+H]⁺: 288.3.

Compound 11: 4-(1-(3-fluorophenyl)-1H-1,2,3-triazole-4-yl)benzene-1,2-diol

Compound 11 was obtained in the form of a yellow solid, and its chemical structure and identification data are as follows:

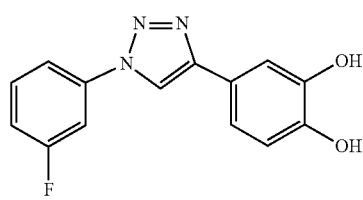 [SMILES: Oc1ccc(-c2cn(-c3cccc(F)c3)nn2)cc1O]

¹H NMR 400 MHZ (MeOD): δ 8.85(s, 1H), 7.76-7.82(m, 2H), 7.65(dd, J=14.4, 6.8 Hz, 1H), 7.36(s, 1H), 7.22-7.33(m, 2H), 6.88(d, J=8.4 Hz, 1H);

Mass (m/z) [M+H]⁺: 272.3.

Compound 12: 4-(1-(3-fluoro-4-methoxyphenyl)-1H-1,2,3-triazole-4-yl)benzene-1,2-diol Compound 12 was obtained in the form of a white solid, and its chemical structure and identification data are as follows:

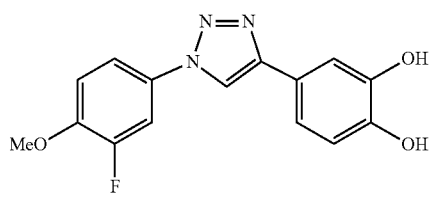 [SMILES: COc1ccc(-n2cc(-c3ccc(O)c(O)c3)nn2)cc1F]

¹H NMR 400 MHZ (MeOD): δ 8.77(s, 1H), 7.77(dd, J=11.6, 2.8 Hz, 1H), 7.68-7.74(m, 1H), 7.32-7.39(m, 2H), 7.24(dd, J=8.0, 2.0 Hz, 1H), 6.88(d, J=8.0 Hz, 1H), 3.98(s, 3H);

Mass (m/z) [M+H]⁺: 302.3.

Compound 13: 4-(1-(2-fluorophenyl)-1H-1,2,3-triazole-4-yl)benzene-1,2-diol

Compound 13 was obtained in the form of a light yellow solid, and its chemical structure and identification data are as follows:

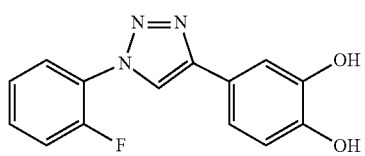 [SMILES: Oc1ccc(-c2cn(-c3ccccc3F)nn2)cc1O]

¹H NMR 400 MHZ (MeOD): δ 8.60(s, 1H), 7.91(td, J=7.6, 1.6 Hz, 1H), 7.58-7.66(m, 1H), 7.43-7.52(m, 2H), 7.36(d, J=2.0 Hz, 1H), 7.25(dd, J=8.4, 2.4 Hz, 1H), 6.88(d, J=8.4 Hz, 1H);

Mass (m/z) [M+H]⁺: 272.3.

Compound 14: 4-(1-(2,3-difluoro-4-hydroxyphenyl)-1H-1,2,3-triazole-4-yl)benzene-1,2-diol Compound 14 was obtained in the form of an ocher solid, and its chemical structure and identification data are as follows:

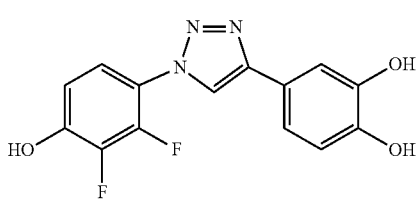 [SMILES: Oc1ccc(-c2cn(-c3ccc(O)c(F)c3F)nn2)cc1O]

¹H NMR 400 MHZ (MeOD): δ 8.51(d, J=2.0 Hz, 1H), 7.45(ddd, J=8.8, 7.7, 2.4 Hz, 1H), 7.34(d, J=2.0 Hz, 1H), 7.23(dd, J=8.0, 2.0 Hz, 1H), 6.95(ddd, J=13.2, 8.4, 2.4 Hz, 1H), 6.87(d, J=8.4 Hz, 1H);

Mass (m/z) [M+H]⁺: 306.2.

Preparation Example 2

2-1. Preparation of the Compound of Formula 1 Based on Chemical Equation 2

Compounds 15 to 17 belonging to Formula 1 of the present disclosure can be prepared according to the following Chemical Equation 2:

[Chemical Equation 2]

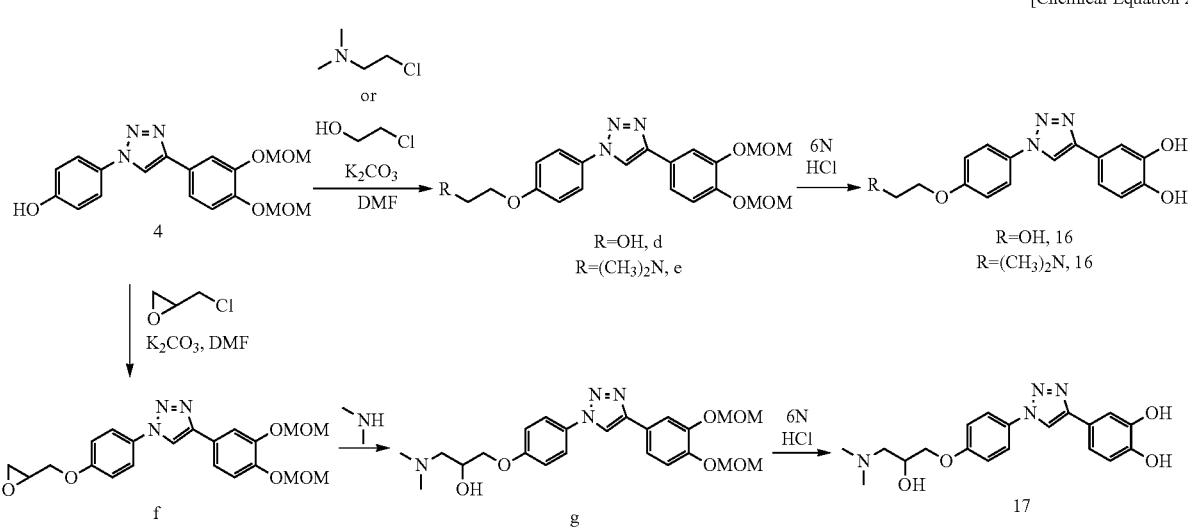

After performing the reaction of adding various alkylamines including epoxide, alkylamine, alcohol functional groups to Compound 4 obtained through Chemical Equation 1, an aqueous acid solution such as hydrochloric acid is added under methanol solvent conditions, and the protecting groups are deprotected at room temperature or 50° C. to obtain the final products Compounds 15 to 17.

2-2. Preparation of Compound 16 Based on Chemical Equation 2

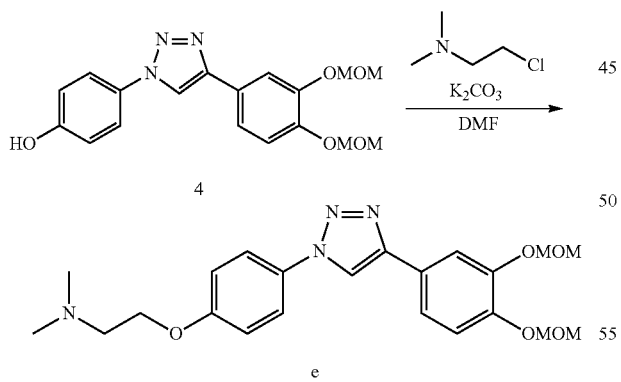

After dissolving Compound 4 (100 mg, 0.28 mmol) in dimethylformamide (2 ml), potassium carbonate (154 mg, 1.12 mmol) and 2-chloro-N,N-dimethoxyethane-1-amine (80 mg, 0.56 mmol) were added, followed by heating and stirring at 110° C. for 5 hours. After checking the completion of the reaction, it was cooled at room temperature and distilled under reduced pressure. And, the filtrate was purified under normal phase column conditions (ethyl acetate: hexane=2:1). Compound e was obtained in the form of a light yellow solid (80 mg, 67% yield), and then Compound 16 was obtained through a deprotection process.

The chemical structure and identification data of Compounds 15 to 17 obtained are as follows.

Compound 15: 4-(1-(4-(2-hydroxyethoxy)phenyl)-1H-1,2,3-triazole-4-yl)benzene-1,2-diol Compound 15 was obtained in the form of a white solid, and its chemical structure and identification data are as follows:

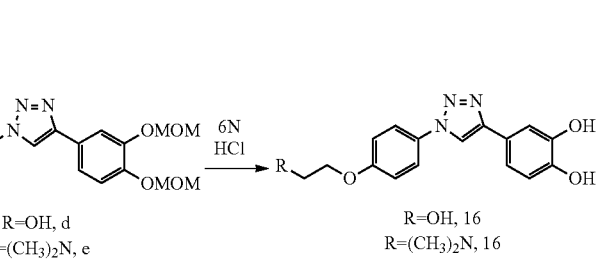

$^1$H NMR 400 MHZ (MeOD): δ 8.64(s, 1H), 7.81(d, J=9.2 Hz, 2H), 7.35(d, J=2.0 Hz, 1H), 7.24(dd, J=8.4, 2.0 Hz, 1H), 7.18(d, 8.8 Hz, 2H), 6.87(d, 8.0 Hz, 1H), 4.15(t, 4.8 Hz, 2H), 3.93(t, 4.8 Hz, 2H);

Mass (m/z) [M+H]$^+$: 314.3.

Compound 16: 4-(1-(4-(2-(dimethylamino)ethoxy)phenyl)-1H-1,2,3-triazole-4-yl)benzene-1,2-diol Hydrochloride Compound 16 was obtained in the form of a white solid, and its chemical structure and identification data are as follows:

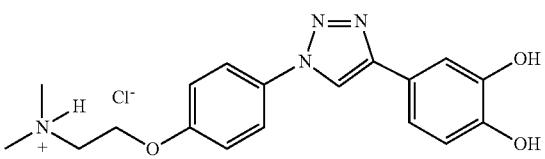

$^1$H NMR 400 MHZ (MeOD): δ 8.63(s, 1H), 7.87(d, J=8.8 Hz, 2H), 7.35(d, J=2.4 Hz, 1H), 7.23-7.27(m, 3H), 6.87(d, 8.4 Hz, 1H), 6.87(d, 8.0 Hz, 1H), 4.35-4.45(m, 2H), 3.35-3.45(m, 2H), 2.89(s, 6H);

Mass (m/z) [M+H]$^+$: 341.4.

Compound 17: 4-(1-(4-(3-(dimethylamino)-2-hydroxypropoxy)phenyl)-1H-1,2,3-triazole-4-yl)benzene-1,2-diol Hydrochloride Compound 17 was obtained in the form of a light yellow solid, and its chemical structure and identification data are as follows:

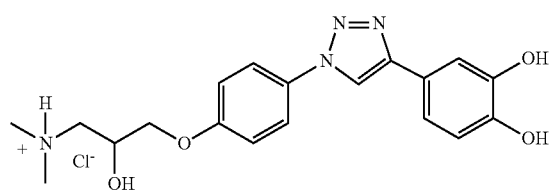

$^1$H NMR 400 MHZ (MeOD): δ 8.71(s, 1H), 7.86(d, J=9.2 Hz, 2H), 7.35(d, J=2.0 Hz, 1H), 7.24(dd, 8.0, 2.0 Hz, 1H), 7.21(d, 9.2 Hz, 2H), 6.88(d, 8.4 Hz, 1H), 4.35-4.45(m, 1H), 4.13(d, 4.8 Hz, 2H), 3.40(d, 3.37-3.43(m, 2H), 3.01(s, 3H), 2.98(s, 3H);

Mass (m/z) [M+H]$^+$: 371.4.

Preparation Example 3

3-1. Preparation of the Compound of Formula 1 Based on Chemical Equation 3

Compounds 18 to 19 belonging to Formula 1 of the present disclosure can be prepared according to the following Chemical Equation 3:

Compound j can be obtained by Click reaction from Compound h and Compound i prepared through commonly known methods. More specifically, it can be obtained by adding a catalytic amount of Cu ion and a reducing agent (for example, sodium ascorbate) under a certain ratio of water and quaternary butyl alcohol solvent conditions, and performing the reaction for 8 to 24 hours at room temperature. Compound k or Compound 1 can be obtained by reacting the ester functional group of Compound j with various alkylamines including a dialkylamine group at high temperature.

And then, the final products Compounds 18 to 19 can be obtained through a deprotection process.

3-2. Preparation of Compound 18 Based on Chemical Equation 3

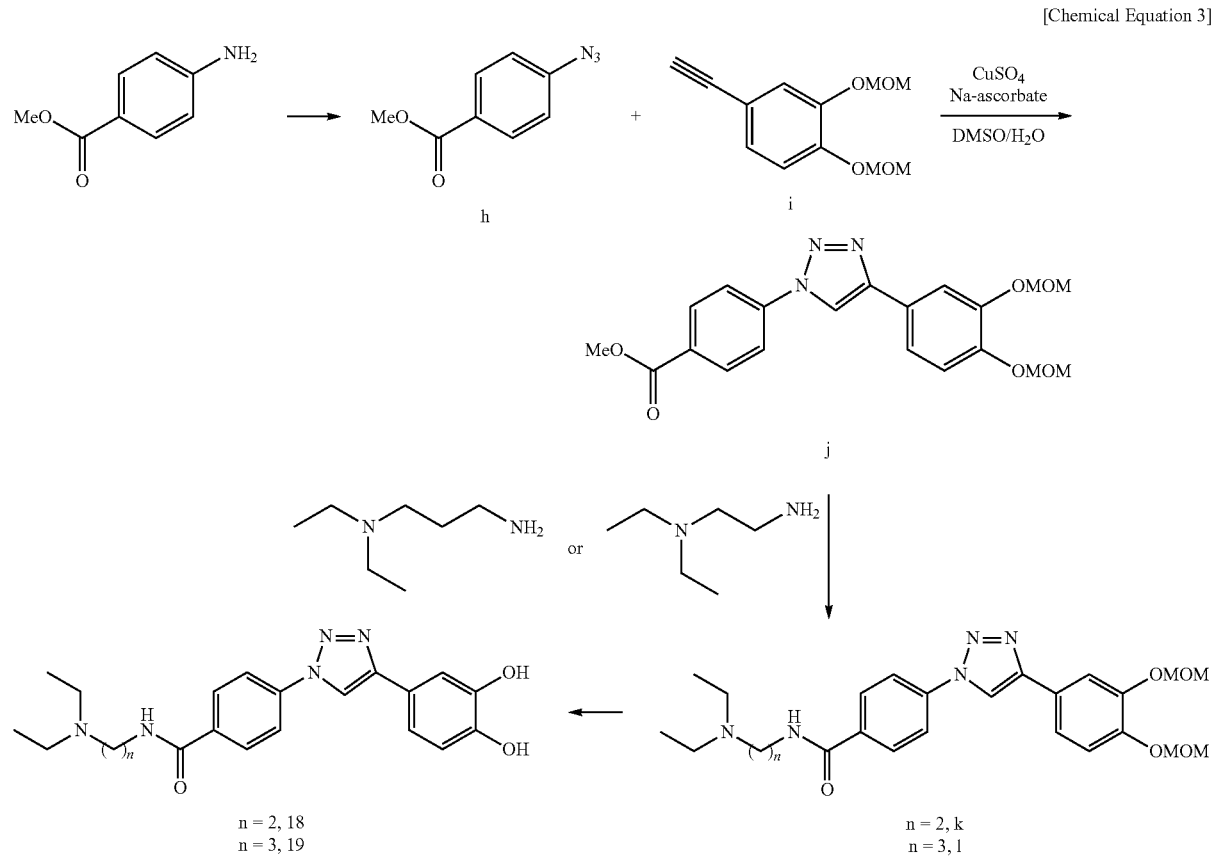

[Chemical Equation 3]

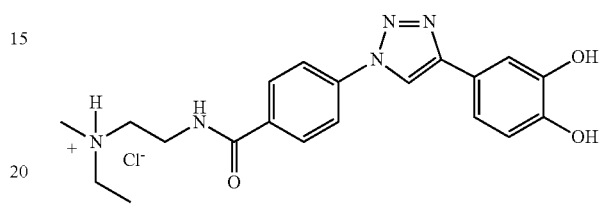

And, the filtrate was purified under normal phase column conditions (dichloromethane:methyl alcohol=10:1). Compound k was obtained in the form of a white solid (90 mg, 74% yield), and then Compound 18 was obtained through a deprotection process.

The chemical structure and identification data of Compounds 18 to 19 obtained are as follows.

Compound 18: N-(2-(diethylamino)ethyl)-4-(4-(3,4-dihydroxyphenyl)-1H-1,2,3-triazole-1-yl)benzamide Hydrochloride Compound 18 was obtained in the form of a white solid, and its chemical structure and identification data are as follows:

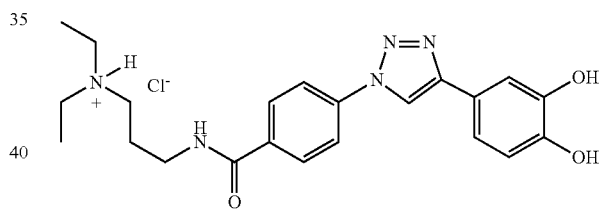

$^1$H NMR 400 MHZ (MeOD): δ 8.85(s, 1H), 8.12(dd, J=13.2, 9.2 Hz, 4H), 7.38(d, J=2.0 Hz, 1H), 7.27(dd, J=8.4, 2.0 Hz, 1H), 6.88(d, 8.4 Hz, 1H), 3.81(t, 6.4 Hz, 2H), 3.44(t, 6.4 Hz, 2H), 4.35-4.42(m, 4H), 1.39(t, 6.8 Hz, 6H);

Mass (m/z) [M+H]$^+$: 396.5.

Compound 19: N-(3-(diethylamino)propyl)-4-(4-(3,4-dihydroxyphenyl)-1H-1,2,3-triazole-1-yl)benzamide Hydrochloride Compound 19 was obtained in the form of a white solid, and its chemical structure and identification data are as follows:

Methyl 4-azidobenzoate (h) (200 mg, 1.12 mmol) and 4-ethynyl-1,2-beads (methoxymethoxy)benzene (i) (248 mg, 1.12 mmol) that can be easily prepared by conventional methods were dissolved in a solvent of a 1:1 ratio of quaternary butyl alcohol and water (2 mL/2 mL). And then, cooper sulfate (17 mg, 0.11 mmol) and sodium ascorbate (43 mg, 0.22 mmol) were added, and stirred for 12 hours at room temperature. After checking the completion of the reaction, extraction was performed using ethyl acetate (10 mL×2) and distilled water (10 mL). The extracted organic layer was dried with anhydrous sodium sulfate, filtered, and then distilled under reduced pressure. And, the filtrate was purified under normal phase column conditions (ethyl acetate: hexane=2:1). Compound j was obtained in the form of a white solid (310 mg, 70% yield).

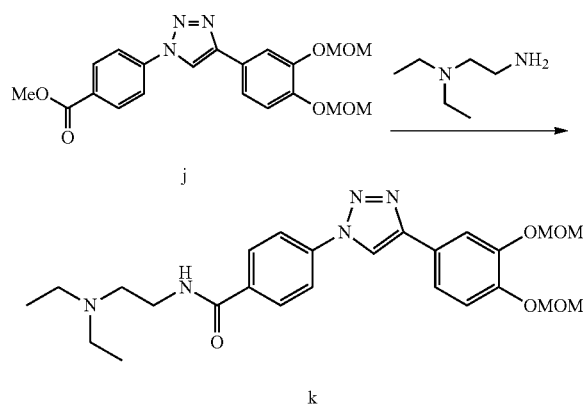

After adding a solvent amount (1.5 ml) of N1,N1-diethylethane-1,2-diamine to Compound j (100 mg, 0.25 mmol), the mixture was heated and stirred at 120° C. for 2 hours. After checking the completion of the reaction, it was cooled at room temperature and distilled under reduced pressure.

$^1$H NMR 400 MHZ (MeOD): δ 8.85(s, 1H), 8.09(dd, J=13.2, 9.2 Hz, 4H), 7.38(d, J=2.0 Hz, 1H), 7.27(dd, J=8.0, 2.0 Hz, 1H), 6.88(d, 8.4 Hz, 1H), 3.55(t, 6.4 Hz, 2H), 3.20-.3.30(m, 6H), 2.05-2.15(m, 2H), 1.36(t, 7.2 Hz, 6H);

Mass (m/z) [M+H]$^+$: 410.5.

Preparation Example 4

4-1. Preparation of the Compound of Formula 1 Based on Chemical Equation 4

Compounds 20 to 25 belonging to Formula 1 of the present disclosure can be prepared according to the following Chemical Equation 4:

[Chemical Equation 4]

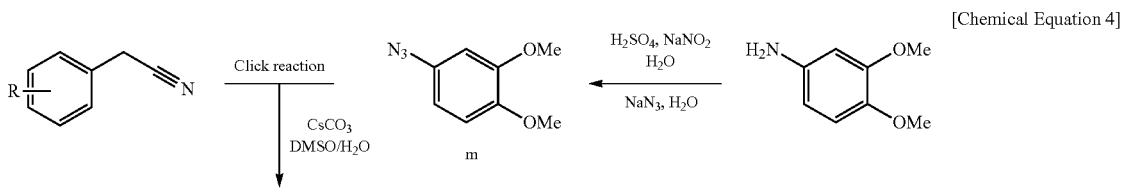

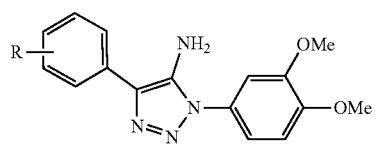
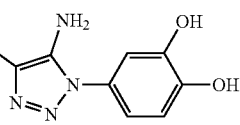

20, 21: R = H
23, 24: R = 4-Cl

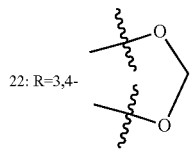

22: R=3,4-

Compounds 20, 22 and 23 can be obtained by Click reaction of commercially purchased benzyl nitrile compound and Compound m prepared through a commonly known method. More specifically, it can be obtained by adding a catalytic amount of cesium carbonate or 1 equivalent of sodium methoxide under a certain ratio of water and dimethyl sulfoxide solvent conditions, and performing the reaction for 2 to 24 hours at room temperature or under reflux conditions. Compound 21 or 24 can be obtained by adding boron tribromide to the aminotriazole Compound 20, 22 or 23 at low temperature and reacting for 1 hour at room temperature to deprotect.

4-2. Preparation of Compound 23 Based on Chemical Equation 4

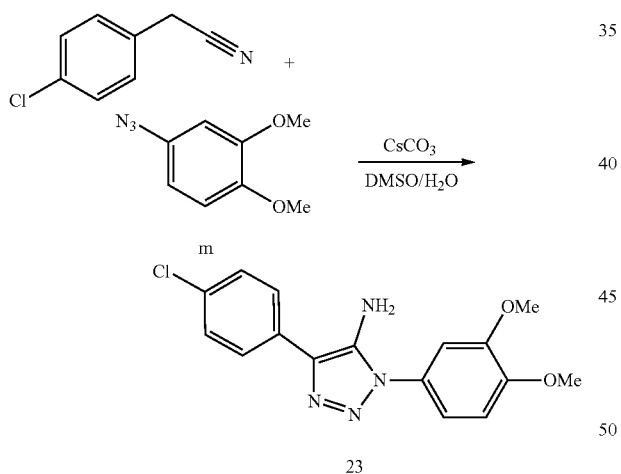

Commercially purchased 2-(4-chlorophenyl)acetonitrile (200 mg, 1.32 mmol) and 4-azido-1,2-dimethoxybenzene (m) (237 mg, 1.32 mmol) prepared by a conventional method were dissolved in a solvent of a 4:1 ratio of dimethyl sulfoxide and water (4 mL/1 mL). And then, cesium carbonate (34 mg, 0.26 mmol) was added and stirred at room temperature for 12 hours. After checking the completion of the reaction, extraction was performed using ethyl acetate (10 mL×2) and distilled water (10 mL). The extracted organic layer was dried with anhydrous sodium sulfate, filtered, and then distilled under reduced pressure. And, the filtrate was purified under normal phase column conditions (ethyl acetate:hexane=1:1). Compound 23 was obtained in the form of a beige solid (320 mg, 73% yield).

4-3. Preparation of Compound 24 Based on Chemical Equation 4

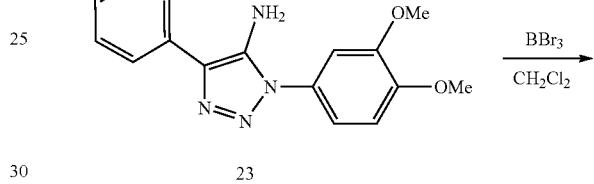

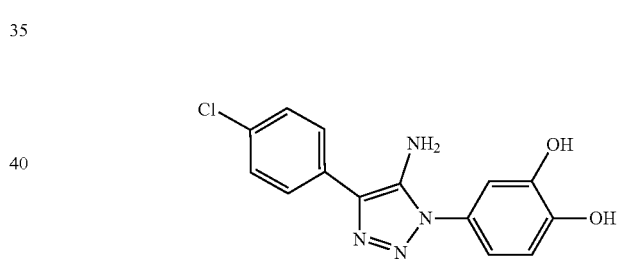

After dissolving Compound 23 (50 mg, 0.15 mmol) in dichloromethane (2 ml), BBr$_3$ (600 μL, 1.0M solution in CH$_2$Cl$_2$, 0.6 mmol) was added at 0° C. And, the temperature was raised to room temperature, and stirred for 1 hour. After checking the completion of the reaction, methanol was added to inactivate the reagent, and distilled under reduced pressure. And, the filtrate was purified under normal phase column conditions (dichloromethane:methyl alcohol=10:1). Compound 24 was obtained in the form of a light orange solid (30 mg, 66% yield).

The chemical structure and identification data of Compounds 20 to 25 obtained are as follows.

Compound 20: 1-(3,4-dimethoxyphenyl)-4-phenyl-1H-1,2,3-triazole-5-amine

Compound 20 was obtained in the form of a light orange solid, and its chemical structure and identification data are as follows:

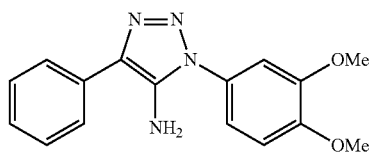 [SMILES: COc1ccc(-n2nnc(-c3ccccc3)c2N)cc1OC]

¹H NMR 400 MHZ (MeOD): δ 7.75(d, J=7.2, Hz, 2H), 7.47(t, 7.2 Hz, 2H), 7.32(tt, J=7.2, 1.2 Hz, 1H), 7.17-7.22(m, 3H), 3.94(s, 3H), 3.92(s, 3H);

Mass (m/z) [M+H]⁺: 297.3.

Compound 21: 4-(5-amino-4-phenyl-1H-1,2,3-triazole-1-yl)benzene-1,2-diol

Compound 21 was obtained in the form of a light green solid, and its chemical structure and identification data are as follows:

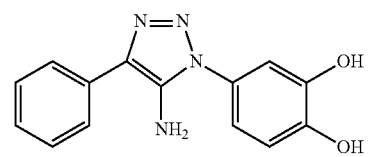 [SMILES: Nc1c(-c2ccccc2)nnn1-c1ccc(O)c(O)c1]

¹H NMR 400 MHZ (MeOD): δ 7.73(d, J=7.2, Hz, 2H), 7.61(t, 7.2 Hz, 2H), 7.14-7.21(m, 3H), 7.53(tt, J=7.6, 1.2 Hz, 1H), 7.08(dd, 8.0, 1.2 Hz, 1H), 7.02-7.05(m, 2H);

Mass (m/z) [M+H]⁺: 269.3.

Compound 22: 4-(benzo[d][1.3]dioxol-5-yl)-1-(3,4-dimethoxyphenyl)-1H-1,2,3-triazole-5-amine Compound 22 was obtained in the form of a light orange solid, and its chemical structure and identification data are as follows:

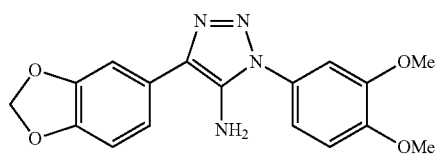 [SMILES: COc1ccc(-n2nnc(-c3ccc4c(c3)OCO4)c2N)cc1OC]

¹H NMR 400 MHZ (MeOD): δ 7.87(s, 1H), 7.23(s, 1H), 7.12-7.22(m, 4H), 6.92(d, 8.0 Hz, 1H), 6.00(s, 2H), 3.94(s, 3H), 3.92(s, 3H);

Mass (m/z) [M+H]⁺: 341.3.

Compound 23: 4-(4-chlorophenyl)-1-(3,4-dimethoxyphenyl)-1H-1,2,3-triazole-5-amine Compound 23 was obtained in the form of a light orange solid, and its chemical structure and identification data are as follows:

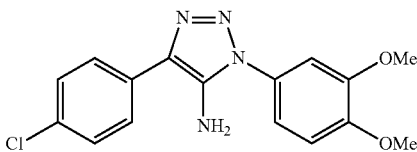 [SMILES: COc1ccc(-n2nnc(-c3ccc(Cl)cc3)c2N)cc1OC]

¹H NMR 400 MHZ (MeOD): δ 7.75(d, J=8.8, Hz, 2H), 7.47(d, 8.8 Hz, 2H), 7.17-7.22(m, 3H), 3.94(s, 3H), 3.92(s, 3H);

Mass (m/z) [M+H]⁺: 331.8.

Compound 24: 4-(5-amino-4-(4-chlorophenyl)-1H-1,2,3-triazole-1-yl)benzene-1,2-diol Compound 24 was obtained in the form of a light orange solid, and its chemical structure and identification data are as follows:

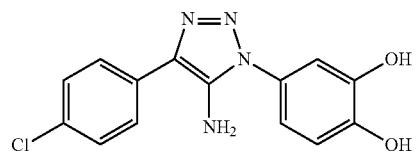 [SMILES: Nc1c(-c2ccc(Cl)cc2)nnn1-c1ccc(O)c(O)c1]

¹H NMR 400 MHZ (MeOD): δ 7.73(d J=7.2 Hz, 2H), 7.46(d, J=7.6 Hz, 2H), 6.95-7.02(m, 2H), 6.90(d, 8.8 Hz, 1H);

Mass (m/z) [M+H]⁺: 303.7.

Compound 25: 4-(5-amino-1-(4-chlorophenyl)-1H-1,2,3-triazole-4-yl)benzene-1,2-diol Compound 25 was obtained in the form of a white solid, and its chemical structure and identification data are as follows:

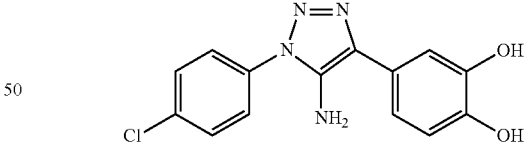

¹H NMR 400 MHZ (MeOD): δ 7.73-7.81(m, 4H), 7.14(d, J=2.0 Hz, 1H), 7.06(dd, 8.4, 2.4 Hz, 1H), 6.99(d, 8.0 Hz, 1H);

Mass (m/z) [M+H]⁺: 303.7.

Preparation Example 5

5-1. Preparation of the Compound of Formula 1 Based on Chemical Equation 5

Compound 26 belonging to Formula 1 of the present disclosure can be prepared according to the following Chemical Equation 5:

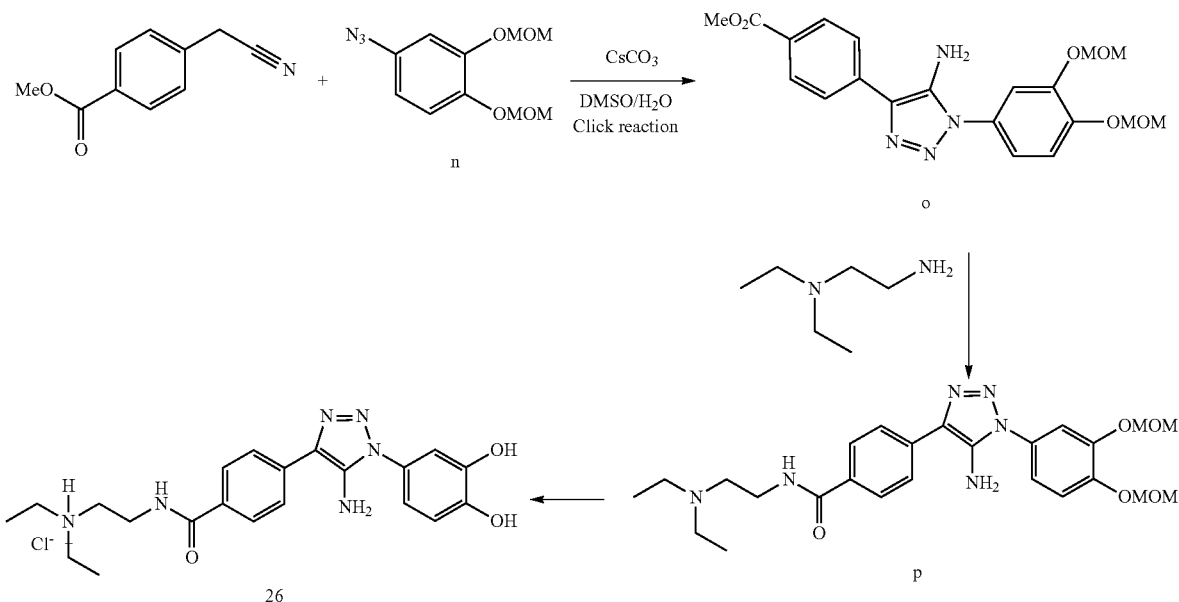

Compound o can be obtained by Click reaction of commercially purchased benzyl nitrile compound and Compound n prepared through a commonly known method. More specifically, it can be obtained by adding a catalytic amount of cesium carbonate or 1 equivalent of sodium methoxide under a certain ratio of water and dimethyl sulfoxide solvent conditions, and performing the reaction for 2 to 24 hours at room temperature or under reflux conditions. Subsequently, Compound p can be obtained by high-temperature reaction using various alkylamines including diethylamine in a solvent amount, and then Compound 26 can be prepared through a deprotection process.

5-2. Preparation of Compound 26 Based on Chemical Equation 5

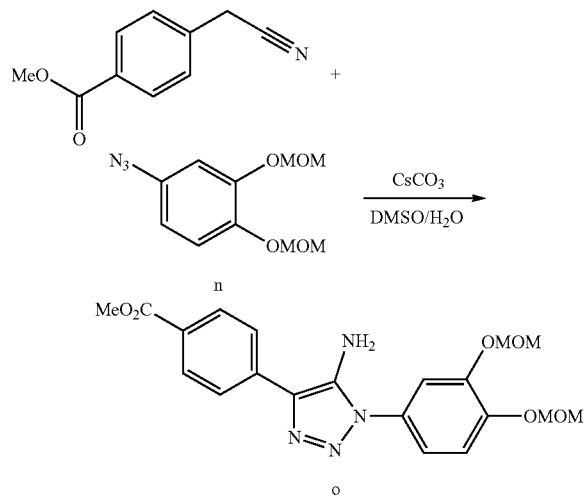

Commercially purchased methyl 4-(cyanomethyl)benzoate (200 mg, 1.14 mmol) and 4-azido-1,2-dimethoxybenzene (n) (272 mg, 1.14 mmol) prepared by a conventional method were dissolved in a solvent of a 4:1 ratio of dimethyl sulfoxide and water (4 mL/1 mL). And then, cesium carbonate (30 mg, 0.26 mmol) was added and stirred at room temperature for 12 hours. After checking the completion of the reaction, extraction was performed using ethyl acetate (10 mL×2) and distilled water (15 mL). The extracted organic layer was dried with anhydrous sodium sulfate, filtered, and then distilled under reduced pressure. And, the filtrate was purified under normal phase column conditions (ethyl acetate:hexane=1:1). Compound o was obtained in the form of a white solid (290 mg, 61% yield).

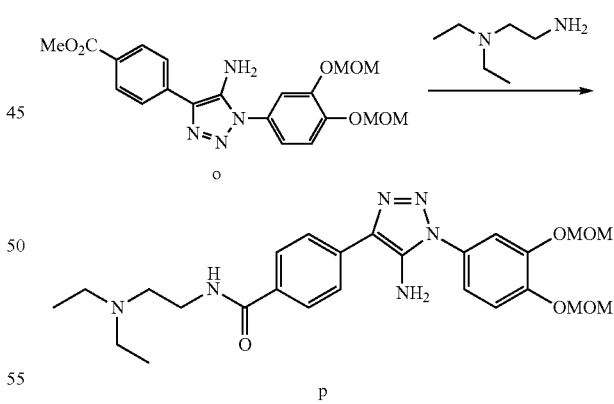

After adding a solvent amount (1.5 ml) of N1,N1-diethylethane-1,2-diamine to Compound o (100 mg, 0.24 mmol), the mixture was heated and stirred at 120° C. for 2 hours. After checking the completion of the reaction, it was cooled at room temperature and distilled under reduced pressure. And, the filtrate was purified under normal phase column conditions (dichloromethane:methyl alcohol=10:1). Compound p was obtained in the form of a white solid (85 mg, 71% yield), and then Compound 26 was obtained through a deprotection process.

The chemical structure and identification data of Compound 26 obtained are as follows.

Compound 26: 4-(5-amino-1-(3,4-dihydroxyphenyl)-1H-1,2,3-triazole-4-yl)-N-(2-(diethylamino)ethyl)benzamide Hydrochloride Compound 26 was obtained in the form of a light green solid, and its chemical structure and identification data are as follows:

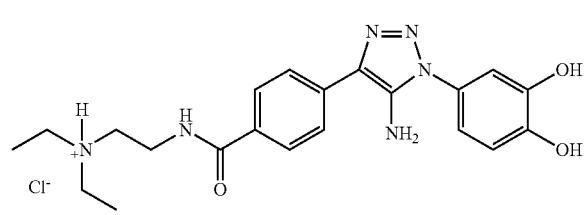

$^1$H NMR 400 MHZ (MeOD): δ 7.88(dd, J=17.6, 8.4 Hz, 4H), 6.93(d, J=8.4 Hz, 1H), 6.76(s, 1H), 6.52(d, 8.4 Hz, 1H), 3.58(t, 6.8 Hz, 2H), 2.90(t, 7.2 Hz, 2H), 2.84(q, J=7.2 Hz, 4H), 1.17(t, 7.2 Hz, 6H);

Mass (m/z) [M+H]$^+$: 411.5.

Example: Adipocyte Differentiation Induction Experiment

In order to prove whether the compounds prepared above can differentiate stem cells or preadipocytes into beige adipocytes, the inventors constructed a cell experimental model. C3H10T1/2 cells exhibit fibroblast morphology when cultured, functionally similar to mesenchymal stem cells.

C3H10T1/2 cells were commercially purchased, and then differentiated into white adipocytes. The differentiated adipocytes were treated with the compounds obtained in the Preparation Examples at a concentration of 20 μM. A group treated with DMSO at a concentration of 20 μM and a group treated with butein at a concentration of 20 μM were used as a control group, respectively. The butein was reported as a material that increases the expression level of UCP1 in US Patent Publication No. US 2015/0374643 A1.

While the UCP1 (uncoupling protein-1) is contained in the mitochondria of brown adipocytes or beige adipocytes, it is difficult to find UCP1 in white adipocytes having little mitochondria. Therefore, by measuring the expression level of UCP1, it is possible to determine whether preadipocytes have differentiated into white adipocytes or otherwise brown adipocytes or beige adipocytes. The higher the expression level of UCP1, the more differentiated preadipocytes into brown adipocytes or beige adipocytes.

The relative expression levels of UCP1 measured by real time PCR are shown in Table 1 below. As a result, the group treated with the triazole derivatives or salt thereof according to the present disclosure showed a remarkably higher expression level of UCP1 compared to the DMSO control group. In addition, the effect was significantly higher than that of butein, which is known to increase the expression level of UCP1.

TABLE 1

| Compound no. | Chemical structure | Relative expression level of UCP1 compared to butein | Relative expression level of UCP1 compared to DMSO |
|---|---|---|---|
| 1 | 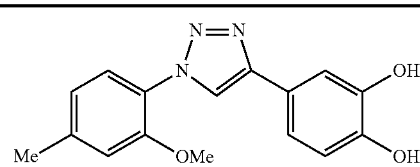 | 12.2 | 3.5 |
| 2 | 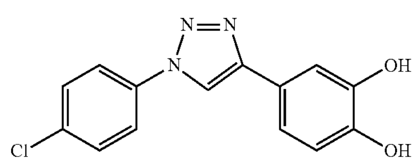 [SMILES: Oc1ccc(-c2cn(-c3ccc(Cl)cc3)nn2)cc1O] | 18.6 | 6.6 |
| 3 | 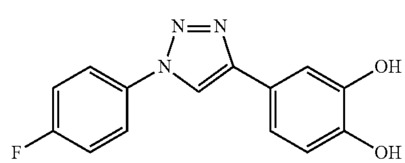 [SMILES: Oc1ccc(-c2cn(-c3ccc(F)cc3)nn2)cc1O] | 34.1 | 12.2 |
| 4 | 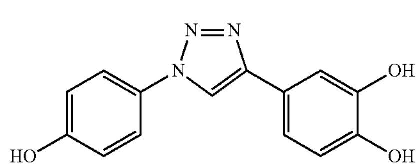 [SMILES: Oc1ccc(-n2cc(-c3ccc(O)c(O)c3)nn2)cc1] | 18.6 | 2.1 |

TABLE 1-continued

| Compound no. | Chemical structure | Relative expression level of UCP1 compared to butein | Relative expression level of UCP1 compared to DMSO |
|---|---|---|---|
| 5 | 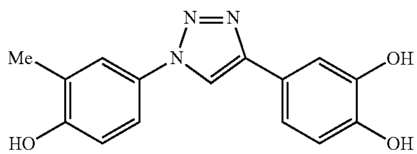 [SMILES: Cc1cc(-n2cc(-c3ccc(O)c(O)c3)nn2)ccc1O] | 20.6 | 2.3 |
| 15 | 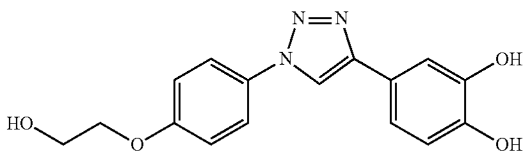 [SMILES: OCCOc1ccc(-n2cc(-c3ccc(O)c(O)c3)nn2)cc1] | 26.9 | 1.6 |
| 16 | 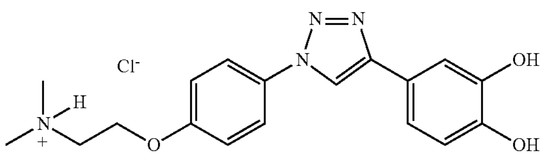 | 37.0 | 2.3 |
| 24 | 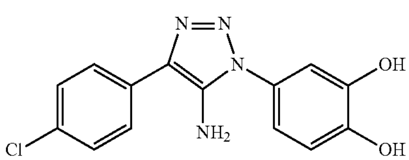 [SMILES: Nc1c(-c2ccc(Cl)cc2)nnn1-c1ccc(O)c(O)c1] | 29.7 | 10.6 |

The compounds of Formula 1 or salts thereof according to the present disclosure was found to have a significantly higher level of UCP1 expression compared to the DMSO control group or the butein control group. Although data of all compounds are not shown in the present specification, those skilled in the art can easily prepare the compounds of Formula 1 or salts thereof based on the above Preparation Examples, and can easily and clearly confirm the effect thereof based on the procedure of the above Example.

What is claimed is:

1. A method for treating, or alleviating one or more selected from the group consisting of obesity, obesity complications, diabetes, dyslipidemia, fatty liver, metabolic syndrome and insulin resistance syndrome comprising administering to a subject in need thereof a compound represented by Formula 1 or a pharmaceutically or sitologically acceptable salt thereof:

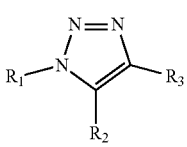

[Formula 1]

wherein
$R_1$ is

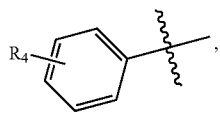

$R_4$ is 1 to 5 substituents each independently selected from the group consisting of a hydrogen atom, a halogen atom, C1-C6 alkyl and —$OR_6$, and is bonded to one or more of ortho, meta and para positions,
$R_6$ is each independently a hydrogen atom, C1-C6 alkyl, C2-C6 alkenyl, C2-C6 alkynyl,

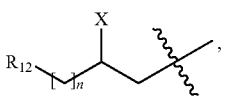

$R_{12}$ is —$N(R_{13})_2$ or —$OR_{13}$, wherein $R_{13}$ is a hydrogen atom or C1-C6 alkyl,
X is a hydrogen atom, and n is 0, 1, 2 or 3,
—$R_2$ is a hydrogen atom or $NH_2$;

—R₃ is

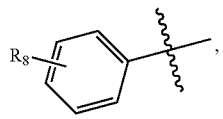

R₈ is 1 to 5 substituents each independently selected from the group consisting of a hydrogen atom, a halogen atom, C1-C6 alkyl and —OH, and is bonded to one or more of ortho, meta and para positions.

2. The method according to claim 1, wherein the compound is represented by Formula 2:

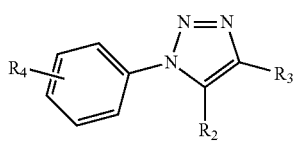

[Formula 2]

wherein R₂, R₃ and R₄ are as described in claim 1.

3. The method according to claim 1, wherein the compound is represented by Formula 3:

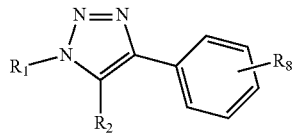

[Formula 3]

wherein R₁, R₂ and R₈ are as described in claim 1.

4. The method according to claim 1, wherein the compound is selected from the group consisting of:
4-(1-(2,4-dimethoxyphenyl)-1H-1,2,3-triazole-4-yl)benzene-1,2-diol;
4-(1-(4-chlorophenyl)-1H-1,2,3-triazole-4-yl)benzene-1,2-diol;
4-(1-(4-fluorophenyl)-1H-1,2,3-triazole-4-yl)benzene-1,2-diol;
4-(1-(4-hydroxyphenyl)-1H-1,2,3-triazole-4-yl)benzene-1,2-diol;
4-(1-(4-hydroxy-3-methylphenyl)-1H-1,2,3-triazole-4-yl)benzene-1,2-diol;
4-(1-(3-fluoro-4-hydroxyphenyl)-1H-1,2,3-triazole-4-yl)benzene-1,2-diol;
4-(1-(3,4-difluorophenyl)-1H-1,2,3-triazole-4-yl)benzene-1,2-diol;
4-(1-(2-fluoro-4-hydroxyphenyl)-1H-1,2,3-triazole-4-yl)benzene-1,2-diol;
4-(1-(4-fluoro-3-hydroxyphenyl)-1H-1,2,3-triazole-4-yl)benzene-1,2-diol;
4-(1-(3-fluorophenyl)-1H-1,2,3-triazole-4-yl)benzene-1,2-diol;
4-(1-(3-fluoro-4-methoxyphenyl)-1H-1,2,3-triazole-4-yl)benzene-1,2-diol;
4-(1-(2-fluorophenyl)-1H-1,2,3-triazole-4-yl)benzene-1,2-diol;
4-(1-(2,3-difluoro-4-hydroxyphenyl)-1H-1,2,3-triazole-4-yl)benzene-1,2-diol;
4-(1-(4-(2-hydroxyethoxy)phenyl)-1H-1,2,3-triazole-4-yl)benzene-1,2-diol;
4-(1-(4-(2-(dimethylamino)ethoxy)phenyl)-1H-1,2,3-triazole-4-yl)benzene-1,2-diol hydrochloride;
1-(3,4-dimethoxyphenyl)-4-phenyl-1H-1,2,3-triazole-5-amine;
4-(5-amino-4-phenyl-1H-1,2,3-triazole-1-yl)benzene-1,2-diol;
4-(4-chlorophenyl)-1-(3,4-dimethoxyphenyl)-1H-1,2,3-triazole-5-amine;
4-(5-amino-4-(4-chlorophenyl)-1H-1,2,3-triazole-1-yl)benzene-1,2-diol; and
4-(5-amino-1-(4-chlorophenyl)-1H-1,2,3-triazole-4-yl)benzene-1,2-diol.

5. The method according to claim 1, wherein the compound or pharmaceutically or sitologically acceptable salt thereof induces or promotes browning of white adipocytes.

6. The method according to claim 5, wherein the white adipocytes are transdifferentiated into beige adipocytes or brown adipocytes.

7. The method according to claim 1, wherein the compound or pharmaceutically or sitologically acceptable salt thereof induces or promotes differentiation of stem cells, embryonic cells or preadipocytes into brown adipocytes or beige adipocytes.

8. The method according to claim 1, wherein the compound or pharmaceutically or sitologically acceptable salt thereof increases the expression of UCP1.

* * * * *